United States Patent [19]
Gauss et al.

[11] 3,990,944
[45] Nov. 9, 1976

[54] MANUFACTURE OF ALCOHOL FROM CELLULOSIC MATERIALS USING PLURAL FERMENTS

[75] Inventors: William Frederick Gauss, Pittsburgh, Pa.; Shuzo Suzuki; Motoyoshi Takagi, both of Toda, Japan

[73] Assignee: Bio Research Center Company Limited, Tokyo, Japan

[22] Filed: Sept. 8, 1975

[21] Appl. No.: 610,731

[30] Foreign Application Priority Data
Sept. 20, 1974   Japan............................... 49-109335

[52] U.S. Cl..................................... 195/33; 195/11
[51] Int. Cl.$^2$..................... C12C 11/08; C12D 3/00
[58] Field of Search ............... 195/33, 111, 115, 13, 195/31 R, 37, 82, 81; 210/11, 2, 3; 426/14, 11, 13, 9

[56] References Cited
UNITED STATES PATENTS

| | | | |
|---|---|---|---|
| 3,711,392 | 1/1973 | Metzger............................ | 195/33 X |
| 3,764,475 | 10/1973 | Mandels et al. ...................... | 195/33 |
| 3,845,218 | 10/1974 | Mussell............................ | 195/37 X |

*Primary Examiner*—A. Louis Monacell
*Assistant Examiner*—Thomas G. Wiseman

[57] ABSTRACT

Alcohol is manufactured from cellulosic materials by a one-step process involving the simultaneous reaction of a cellulosic material, a cellulase and an alcohol-producing microorganism.

4 Claims, No Drawings

MANUFACTURE OF ALCOHOL FROM CELLULOSIC MATERIALS USING PLURAL FERMENTS

BACKGROUND OF THE INVENTION

This invention relates to a method for the production of alcohol in high yields from cellulosic materials as the substrate.

Heretofore, production of alcohol (ethanol) has been attempted by a procedure comprising the steps of reacting a cellulase upon cellulose as the substrate to enzymatically saccharify the cellulose to glucose, and subsequently separately causing the resultant glucose to be reacted upon by an alcohol-producing microorganism to produce alcohol. According to this conventional method, the conversion of cellulose to glucose by a cellulase is low and, consequently, large amounts of unconverted cellulosic residue are obtained. Therefore, if the product of such a cellulase treatment of cellulosic materials is employed as the raw material for alcohol fermentation it is necessary to separate the glucose from said product, for example, by filtration. Thus, in addition to the drawback that the glucose concentration in the saccharified liquid is low due to the low conversion of cellulose to glucose, the production of glucose according to the conventional method includes the possibility that glucose is lost during the aforementioned separation. Consequently, low yields of alcohol are obtained by subjecting the saccharified liquid to fermentation.

SUMMARY OF THE INVENTION

It has now been found that greater yields of alcohol can be obtained from a cellulosic material when there are simultaneously reacted under anaerobic conditions the cellulosic material, a cellulose, and an alcohol-producing microorganism.

DETAILED DESCRIPTION

Although it is not desired to be bound by any theory, it is presently believed that in the conventional saccharification of cellulose to glucose using a cellulase the yields of glucose are low because the reaction is inhibited by the glucose formed as well as by cellobiose obtained as a by-product. It is therefore postulated that the simultaneous presence of an alcohol-producing microorganism with the cellulose in the reaction mixture in accordance with the invention results in the conversion of glucose to alcohol thereby enabling the enzymatic conversion of cellulose to glucose to proceed further than would be the case if the glucose were not so converted. Regardless of any theory, this invention results in the saccharification reaction proceeding smoothly and in a notable increase in the overall yield of alcohol from cellulose.

As described above, this invention is characterized by simultaneously reacting a cellulase and an alcohol-producing microorganism upon a substrate made up of either cellulose or a substance composed preponderantly of cellulose.

The cellulosic substrates which are useful as starting materials for the present invention include purified cellulose, agriculturally produced materials such as cotton, wood, rice straw, wheat straw, maize ears (corn cobs) and other substances composed preponderantly of cellulose such as newspaper, corrugated paper, magazine paper and scrap paper. For these substances to be used effectively as substrates for the saccharification reaction in the presence of cellulase, it is desirable to pulverize or disintegrate them. For the hydrolysis of these cellulosic substrates, use of a commercially available cellulase will suffice. An enzymatic preparation such as, for example, Cellulase Onotsuga may be used. A liquid containing a cellulase, namely a culture liquid from a cellulase-producing microorganism such as, for example, a culture liquid from *Trichoderma viride* may also be used.

As the alcohol-producing microorganism to be simultaneously used with the cellulase, there can be employed such microorganisms as, for example, *Saccharomyces cerevisiae* and *Rhizopus Javanicus* which have heretofore been used for the conversion of glucose into ethanol.

In order for the cellulosic substrate to be simultaneously reacted upon by a cellulase and an alcohol-producing microorganism, an aqueous suspension containing from 1 to 30% by weight of cellulose or a substance composed predominantly of cellulose is prepared and thermally sterilized so as to serve as the substrate, a cellulase (or a cellulase-containing liquid) is added to the substrate and at the same time, an alcohol-producing microorganism cultured in advance is added thereto so that the reaction will proceed anaerobically at temperatures of from about 25° to about 35° C.

When the reaction is carried out as described above, as illustrated by a preferred embodiment described below, the production of alcohol in a yield approximately four times as high as the described conventional method becomes possible. The production of alcohol from cellulose by this method has an additional advantage in that it is carried out in a simple one-step operation. To be more specific, in contrast with the conventional method wherein there are involved the two steps of saccharifying a cellulosic substrate with a cellulase and separating the saccharification product by filtration and subsequently subjecting the saccharified liquid filtrate to alcohol fermentation, the present invention effects the saccharification reaction of a cellulosic substrate with a cellulase and the alcohol fermentation of the glucose formed by the saccharification reaction simultaneously in one step. Thus, the operation involved in the present invention is highly efficient.

Since alcohol is efficiently produced by the present invention from cellulose or from agriculturally produced materials or wastes composed preponderantly of cellulose, as described above, this invention is not only highly advantageous for the production of alcohol but also for the effective utilization of cellulosic resources.

DESCRIPTION OF PREFERRED EMBODIMENTS

The present invention will now be described specifically with reference to preferred embodiments which should not be construed as limiting the spirit and scope of this invention.

EXAMPLE 1

A substrate was prepared by suspending 12.5 g of pulp obtained from wood (having 80% by weight of cellulose content) in 100 g of water containing in solution 0.25 g asparagine as a nitrogen source, 0.1 g potassium hydrogen phosphate ($KH_2PO_4$), 0.3 g magnesium sulfate ($MgSO_4 \cdot 7H_2O$) and 0.02 g yeast extract. The resultant mixture was adjusted to pH 4.0 by addition of an acetate buffer and then thermally sterilized. To the above mixture, there were added 1 g of refined commercially available cellulase and two platinum loopfuls of *Saccharomyces cerevisiae* mycelium directly from an agar slant thereof, and the mixture was allowed to react at about 30° C. for 96 hours. When the reaction mixture was analyzed at this point, formation of 2 g of alcohol in the substrate was confirmed. When the reaction was continued for a further 96 hours, there were eventually formed 4 g of alcohol.

By way of comparison, production of alcohol was carried out by the procedure described below in accordance with the conventional two-step method.

To a substrate suspension of wood pulp in water in the amounts described above, 1 g of the same refined commercially available cellulase was added and the mixture allowed to react at 40° C. for 96 hours. The amount of reducing sugar formed in the resultant saccharified liquid was 5 g, 60% (3 g) of which was cellobiose and the remaining 2 g was glucose. When reaction was continued for an additional 96 hours, no change was observed in the amount of reducing sugar produced. The saccharified liquid thus produced was mixed with the same nitrogen source, phosphate and other inorganic salts as above and the resultant mixture was thermally sterilized. *Saccharomyces cerevisiae* was added to the mixture which was then allowed to ferment. The amount of alcohol formed after completion of fermentation fell short of 1 g.

In this case, since the glucose content in the saccharified liquid as the alcohol fermentation substrate was 2 g, the theoretical maximum yield of alcohol would have been 1 g.

EXAMPLE 2

This example illustrates the use in the process of this invention of a cellulase enzyme complex elaborated by *Trichoderma viride*.

In two separate shake flasks *Trichoderma viride* QM 9414 (ATCC 26,921) was aerobically cultivated at 30° C. for a period of 6 days. Each flask contained 100 ml of an identical conventional nutrient medium containing cellulose powder as the carbon source. During cultivation the pH was adjusted to 5.4 twice a day. At the end of the 6 day period, the contents of one of the flasks (A) was filtered to obtain a culture filtrate containing the cellulose enzyme complex; the contents of the other flask (B) was left unfiltered. Both cellulase containing materials were then used in the process of this invention as described below.

Five g each of sterilized cellulose powder (300 mesh, containing 95% by weight of cellulose) were separately placed aseptically into two sterilized 100 ml flasks. Into one of these flasks (C) there was added 45 ml of the above culture filtrate from flask (A). Into the other flask (D) there was added 45 ml of the above well-stirred unfiltered culture broth from flask (B), that is, the entire aqueous culture mass without separation of any component thereof (whole culture broth). Next there was added to each of flasks (C) and (D) 5 ml of a sterilized solution containing the following ingredients:

| | |
|---|---|
| Asparagine | 125 mg |
| KH$_2$PO$_4$ | 50 mg |
| MgSO$_4$ · 7H$_2$O | 150 mg |
| Yeast extract | 10 mg |
| Distilled water | 5 ml |

The resulting mixtures in each flask were adjusted to pH 4.0 as necessary. Thereafter *Saccharomyces cerevisiae* was added to each flask, as in Example 1, and the mixture reacted anaerobically. After reaction for 96 hours, the reaction mixture in each flask was analyzed. In the mixture from flask (C) 1.2 g ethanol was observed; in that from flask (D) 1.4 g. When the reaction was continued for another 96 hours, the mixture from flask (C) contained 2.0 g ethanol, and that from flask (D) contained 2.3 g.

Since in the above Example 2, the cellulosic substrate was employed in an amount of 4.75 g cellulose content, whereas in Example 1 the cellulosic substrate was employed in an amount of 10 g cellulose content, it will be seen that the improvements in the amounts of ethanol produced in the respective examples are of the same order of magnitude. Surprisingly, however, a comparison of the results obtained using the whole culture broth [flask (D)] as the cellulase source with the results obtained using the culture filtrate [flask (C)] as the cellulase source, shows a marked further improvement in the amounts of ethanol obtained, 2.3 g as opposed to 2.0 g, an increase of 15%.

The use of a whole culture broth as the enzyme source in the enzymatic saccharification of a cellulosic substrate is described and claimed in copending application Ser. No. 572,428, filed Apr. 28, 1975, and assigned to the same assignee as the present application. The earlier application, incorporated herein by reference, discloses cultivation of a cellulolytic microorganism, such as *Trichoderma viride*, in an aqueous nutrient medium in the presence of a cellulosic material in shake flasks or by submerged culture. The entire aqueous culture mass so obtained, or an aliquot thereof, without separation of any component, is then used as the enzyme source in the saccharification of cellulose.

It is seen from the foregoing that the present invention achieves production of alcohol in yields remarkably greater than those obtainable by the conventional two-step method.

What is claimed is:

1. In the manufacture of alcohol from a cellulosic material, wherein the cellulosic material is enzymatically saccharified to glucose by a separately prepared cellulase and the glucose is fermented in the presence of an alcohol-producing microorganism to obtain alcohol, the improvement which comprises:
    simultaneously reacting under anaerobic conditions said cellulosic material, said separately prepared cellulase and said alcohol-producing microorganism, whereby greater yields of alcohol are obtained.

2. The process of claim 1, wherein the reaction is carried out at a temperature of 25° to 35° C.

3. The process of claim 2, wherein the cellulase is derived from *Trichoderma viride* and the alcohol-producing microorganism is *Saccharomyces cerevisiae*.

4. The process of claim 1, wherein the cellulase is derived from the cultivation of a cellulolytic microorganism in an aqueous nutrient medium in the presence of a cellulosic material and is used in the form of the entire aqueous culture broth obtained in such cultivation or an aliquot thereof without separation of any component.

* * * * *